US008857470B2

(12) United States Patent
Rahimy et al.

(10) Patent No.: US 8,857,470 B2
(45) Date of Patent: Oct. 14, 2014

(54) CONNECTION DEVICE FOR CONNECTING A FIRST RESERVOIR WITH A SECOND RESERVOIR

(75) Inventors: Ismael Rahimy, Friedberg (DE); Torsten Brandenburger, Reichelsheim (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 70 days.

(21) Appl. No.: 13/356,180

(22) Filed: Jan. 23, 2012

(65) Prior Publication Data

US 2012/0192976 A1 Aug. 2, 2012

Related U.S. Application Data

(60) Provisional application No. 61/435,800, filed on Jan. 25, 2011.

(30) Foreign Application Priority Data

Jan. 25, 2011 (EP) .................................... 11151942

(51) Int. Cl.
*F16L 37/05* (2006.01)
*A61M 39/26* (2006.01)
*A61J 1/20* (2006.01)

(52) U.S. Cl.
CPC ........ *A61J 1/2089* (2013.01); *A61J 2001/2031* (2013.01); *A61J 2200/10* (2013.01); *A61J 2001/2051* (2013.01); *A61J 2001/201* (2013.01); *A61J 2001/2055* (2013.01); *Y10S 604/905* (2013.01)
USPC ......... 137/798; 251/149.4; 604/256; 604/905

(58) Field of Classification Search
USPC ................................ 137/317, 318, 798, 614, 137/614.03–614.05; 251/149.1, 149.5, 251/149.4; 604/249, 256, 905
See application file for complete search history.

(56) References Cited

U.S. PATENT DOCUMENTS

| | | | | |
|---|---|---|---|---|
| 2,712,322 | A * | 7/1955 | Fortin | 137/318 |
| 2,954,768 | A | 10/1960 | Hamilton | |
| 3,024,044 | A * | 3/1962 | Benevento | 137/318 |
| 4,373,559 | A | 2/1983 | Mowles et al. | |
| 5,833,213 | A * | 11/1998 | Ryan | 251/149.1 |
| 6,022,339 | A | 2/2000 | Fowles et al. | |
| 6,258,078 | B1 * | 7/2001 | Thilly | 604/256 |
| 6,669,673 | B2 * | 12/2003 | Lopez | 604/249 |
| 2002/0022804 | A1 | 2/2002 | Connolly et al. | |
| 2007/0289668 | A1 | 12/2007 | Costanzo | |

FOREIGN PATENT DOCUMENTS

| | | |
|---|---|---|
| DE | 19930791 | 1/2001 |
| EP | 0765651 | 4/1997 |
| EP | 1066812 | 6/2000 |
| EP | 1859773 | 11/2007 |
| WO | 96/40327 | 12/1996 |

* cited by examiner

*Primary Examiner* — Kevin Lee
(74) *Attorney, Agent, or Firm* — Occhiuti & Rohlicek LLP

(57) ABSTRACT

A connection device for connecting a first reservoir with a second reservoir, includes a first section for arranging the first reservoir closed with a seal; a second section for arranging the second reservoir; and a piercing element which penetrates with a piercing end the seal of the first reservoir when the first reservoir is arranged at the first section. In some embodiments, the piercing element can be moved from a first position into a second position, wherein it blocks in the first position a flow connection between the first and the second section, while in the second position it allows for a flow connection between the first and the second section.

23 Claims, 5 Drawing Sheets

FIG 2A
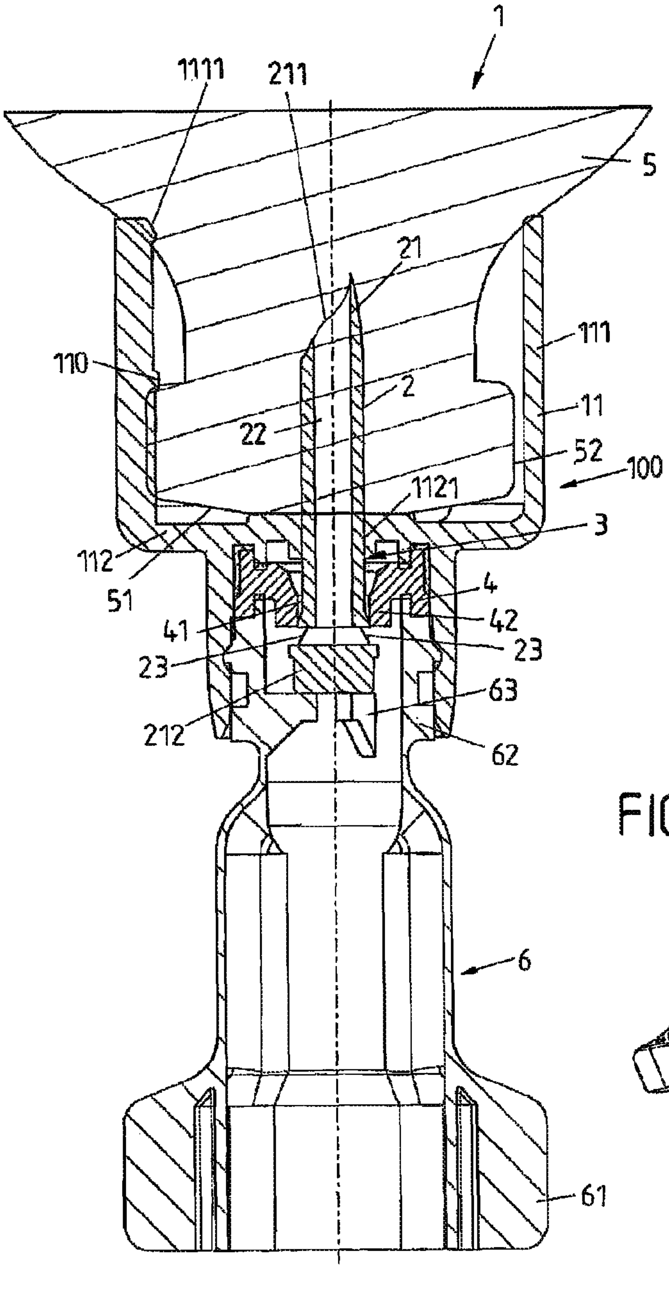
FIG 2B
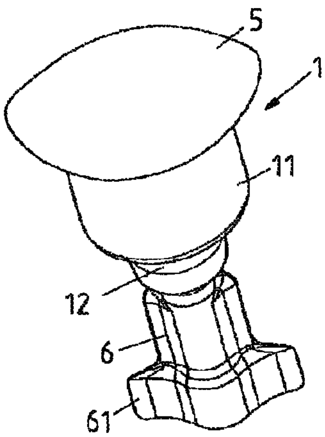
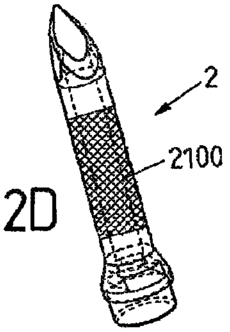
FIG 2D
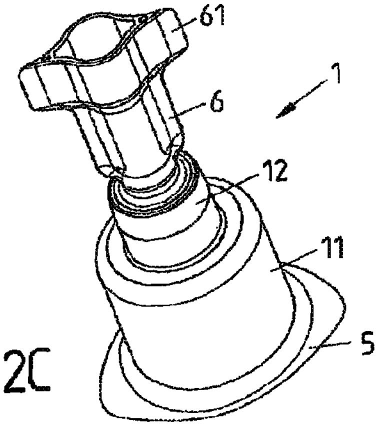
FIG 2C

CONNECTION DEVICE FOR CONNECTING A FIRST RESERVOIR WITH A SECOND RESERVOIR

CROSS REFERENCE TO RELATED APPLICATIONS

This application claims priority to U.S. Provisional Application No. 61/435,800, filed on Jan. 25, 2011, and European Application No. 11151942.7, filed on Jan. 25, 2011. The contents of the foregoing applications are incorporated herein by reference.

The invention concerns a connection device for connecting a first reservoir with a second reservoir according to the preamble of Claim 1.

BACKGROUND

In medical technology connection devices (described as "adapters" or "connectors") are known by means of which a first reservoir, which contains a medicinal active substance, can be connected with a second reservoir, which contains, for example, a liquid, in order to dilute or dissolve the medicinal active substance and transport it into the second reservoir, for example, to mix it with the liquid. The medicinal active substance in the first reservoir, which can have the form of a phial ("vial"), comprises, for example, a powder or fluid. The second reservoir can be designed as a bag (for example, an infusion bag) or as a collapsible, elastic bottle.

For example, the DE 199 30 791 A1 describes a needle adapter, by means of which a first reservoir can be connected with a second reservoir. The needle adapter comprises a hollow needle which is tapered on both ends. By means of said hollow needle, a seal of the first reservoir, as well as a seal of the second reservoir can be penetrated and a flow connection can be formed between the two reservoirs. In the U.S. Pat. No. 6,022,339 A, the flow connection is also formed by means of a hollow needle which is tapered on both ends. Hollow needles are also used as a type of actuator for the purpose of opening and closing a separate valve body (described, for example, in the WO 96/40327 A1). In the EP 0 795 651 A1, for example, such a valve body is provided through a membrane having openings.

SUMMARY

The present invention deals with the problem of providing a connection device, which allows for the most reliable connection between a first and a second reservoir and which allows for the possibility of forming a flow connection with the greatest possible flow diameter between the reservoirs. In particular, it is also important to provide a possibility for resealing the flow connection.

This problem is solved by means of the connection device with the identifying characteristics described below.

Accordingly, the invention provides a connection device for connecting a first and a second reservoir, which has

- a first section for placing, especially connecting the first reservoir, which is closed with a seal;
- a second section for placing, especially connecting the second reservoir, which is closed with a seal; and
- a piercing element, which penetrates with one piercing end the seal of the first reservoir when the first reservoir is arranged at the first section, wherein
- the piercing element comprises a duct and can be moved from a first position into a second position (relative to the first and the second section), wherein

- in the first position the duct of the piercing element is sealed or closed and a flow connection between the first and the second section is blocked, while
- in the second position the duct of the piercing element is released or open and a flow connection between the first and the second section is made possible.

A further feature of the invention is a connection device for connecting a first and a second reservoir with

- a first section for placing the first reservoir, which is closed with a seal;
- a second section for placing (especially connecting) the second reservoir; and
- a piercing element, which penetrates with one piercing end the seal of the first reservoir when the first reservoir is arranged (especially connected) at the first section, wherein
- the piercing element can be moved from a first position into a second position (relative to the first and the second section), wherein, in the first position, the piercing element blocks a flow connection between the first and the second section, while, in the second position, it allows for a flow connection between the first and the second section.

In particular, the piercing element blocks in the first position a flow connection between the first section (or the first reservoir arranged at the first section) and the second reservoir, when said piercing element is arranged at the second section, while in the second position it allows for a flow connection between the first section, or first reservoir, and the second reservoir. The piercing element does not represent an actuator for opening and closing a separate valve body. Instead, the piercing element in itself, or components of the piercing element, represents a valve body, which blocks or releases a flow connection or passage opening.

For example, the piercing element is arranged and designed in such a way that it is moved from the first into the second position when the first reservoir is arranged at the first section. Consequently, after the first reservoir has been put in place a flow connection is formed between the first and the second reservoir (provided the second reservoir is arranged at the second section).

In particular, the piercing end with which the piercing element penetrates the seal of the first reservoir when the first reservoir is arranged at the connection device is designed in form of a needle. In particular the first and the second section are sections of (especially integrally formed) adapter parts, wherein the piercing element is arranged in movable fashion in relation to said adapter part.

In particular, the first section of the connection device is designed in such a way that the first reservoir can be detachably connected with the first section, for example, to receive a first reservoir shaped like a medication container (for example, in the form of a glass or plastic bottle or a phial—"vial"), wherein it is possible to insert into the first section the neck of a medication container provided especially with a seal (for example, in the form of a plastic film or a plug). For example, the first section comprises connection structures (for example, latching structures), by means of which the medication container can be detachably connected with the first section.

It should be noted that it is indeed possible that the first and/or the second reservoir are connected with the connection device not directly but via at least one further element and that said reservoir is connected in detachable manner, which will subsequently be explained in more detail.

When the first reservoir is arranged at the first section of the connection device along an arrangement direction, for example, moved into the first section along the arrangement direction, the piercing end of the piercing element penetrates the seal of the first reservoir. In addition, by means of the mechanical contact of the seal having the piercing element, the piercing element is moved in arrangement direction along with the first reservoir, i.e., in the direction of the second section of the connection device, and is therefore pushed in the direction of the second reservoir, provided the second reservoir is arranged at the second section.

Consequently, when the first reservoir is put in place, the piercing element is moved into the second position (opening position) in which it allows for a flow connection between the two reservoirs. In particular, when the first reservoir is put in place, the piercing element is moved into its second position (for example, exclusively) because of the contact the reservoir seal has with the piercing element. Here it is possible that, when the first reservoir is arranged at the connection device, the piercing end penetrates the seal and produces a movement because of the friction between the section of the seal adjoining the piercing element and the piercing element.

However, it is also possible that initially the seal of the reservoir is not or only partially penetrated by the piercing element but, when the first reservoir is arranged at the connection device, the seal of the reservoir pushes against the piercing element and, as a result, the piercing element is moved in the direction of the second position. In particular, the connection device has a limit stop which defines the second position of the piercing element, wherein the piercing element is pushed against the limit stop when, for example, the first reservoir is put in place and only when the first reservoir is moved the piercing end of the piercing element penetrates the seal.

Consequently, when the first reservoir is arranged at the connection device, it is possible to mix (or dissolve) the substance (especially in the form of a powder or a liquid) contained in the first reservoir with the substance (especially in the form of a liquid) contained in the second reservoir. It is also possible that the second or the first reservoir is empty and only a transport from one reservoir into the other takes place.

In particular, the invention-based connection device makes it possible to connect in a most reliable and easy way two medical containers, especially connecting a medication container (as mentioned above) with a medical bag (for example, an infusion, a transfusion, or nourishment bag). The flow connection to the second reservoir does not take place via a second needle of the piercing element but by means of a valve which moves the piercing element into an opening position. As a result, a larger flow diameter on the part of the second section of the connection device can be achieved and thus an altogether larger flow between the two reservoirs so as to allow for the fastest possible.

In particular, the piercing element is moved into the second position when, as a result, the first reservoir is arranged at the first section, so that it is brought into an end position relative to the first section, wherein the piercing element is designed in such a way that it can be moved back into the first reservoir when the first reservoir is moved out of the end position and away from the second section of the connection device, for example, removed from the first section.

Consequently, the piercing element is taken along when the first reservoir is moved in the opposite direction. As a result, for example, when removing the first reservoir, the flow connection between the first and the second section of the connection device is closed again, thus counteracting the possibility that a substance contained in the second reservoir could escape when the first reservoir is removed or preventing such possibility altogether. However, it is not necessarily required to completely remove the first reservoir from the first section of the connection device to return the piercing element to its first position (the locking position). For example, it is possible to move the first reservoir from the end position merely to a standby position in which it still has a certain connection with the first section, but the piercing element has already been moved to locking position, thus disabling the flow connection between the first and the second reservoir.

For example, the piercing element is arranged in movable fashion in a passage opening of the connection device relative to the first and/or second section. As a result, it is moved relative to the first and/or second section when the first reservoir is arranged (i.e., when a mechanical contact exists between the seal of the first reservoir and the piercing element). The subsequent description includes possible embodiments of the passage opening.

According to a further model of the invention, the piercing element forms a channel by means of which a flow connection is formed between the first and the second section of the connection device, i.e., between the first and the second reservoir, when the piercing element is in the second position. Here a marginal section of the above-mentioned passage opening adjoins the piercing element in such a way that it blocks via the channel of the piercing element a flow connection between the first and the second section when the piercing element is in the first position.

For example, the channel is designed as a cavity stretching across the interior of the piercing element and extending from an entry opening located in the area of the piercing end of the piercing element to at least one exit opening. In the first position of the piercing element the marginal section of the passage opening blocks the passage between the exit opening and the second section of the connection device. The piercing element can have the design of a cannula which has an entry opening that is located at the front end of the pointed piercing end so that after piercing the seal of the first reservoir the entry opening is situated inside the first reservoir. If now the piercing element is in opening position, the substance in the first reservoir can be transported via its entry opening into the cavity of the piercing element and via its exit opening into the second section of the connection device and into the second reservoir.

The marginal section of the passage opening adjoins an outer surface of the piercing element. When the piercing element is in closed position, said marginal section does not directly have to cover the exit opening. The exit opening of the piercing element can also be designed in such a way that, when the piercing element is in closed position (in the first position), the exit opening is situated on a side of the adjoining marginal section of the passage opening which faces the piercing end of the piercing element (i.e., the first reservoir). This means that the marginal section of the passage opening, which adjoins as close as possible the piercing element, does not cover the exit opening directly but it still prevents substance in the first reservoir from traveling in the direction of a second reservoir arranged at the second section of the connection device.

In the second position of the piercing element, the exit opening is located on a side of the marginal section of the passage opening adjoining the piercing element which faces away from the piercing end (i.e., the first reservoir). As a result, a substance is no longer blocked from passing from the exit opening of the piercing element into the second section and into the second reservoir.

In one embodiment of the invention, the piercing element is designed as an at least in sections hollow body, for example, as a tube. Basically, the piercing element can be designed in the form of a hollow cylinder, wherein the exit opening basically runs in radial direction. For example, the exit opening is inserted in the casing of a hollow body. The exit opening can extend in sections across the circumference of the piercing element, for example a hollow body. In particular, the end of the piercing element spaced from the piercing end is closed, i.e., the front end of the piercing element facing away form the piercing end has no opening. In particular, the piercing element has several, preferably radial exit openings. However, as subsequently explained, it is also possible to have exit openings with different designs.

In the context of this embodiment, the invention can be described also in that the piercing element comprises an exit opening and can be moved from a first position into a second position, wherein in the first position the exit opening of the piercing element is closed and a flow connection between the first and the second section is blocked, while in the second position the exit opening of the piercing element is released or open and a flow connection between the first and the second section is made possible.

It should be noted that it is not absolutely necessary that the piercing element is designed in the form of a cannula, i.e., that it has a channel in the form of a hollow body. Instead, it is also possible that the channel, by means of which a substance can be transported from the first section (from the first reservoir) into the second reservoir, is designed as a recess in an outer surface of the piercing element. In particular, the piercing element can involve a solid (especially longitudinal) body which comprises at its outer surface a groove that extends along the longitudinal axis of the body. By means of said solid body the substance from the first section of the connection device can be transported into the second section of the connection device.

In particular, the blocking of such a channel in the first position of the piercing element is achieved in that a marginal section of the passage opening on the side of the groove facing the second section of the connection device adjoins closely the piercing element, thus preventing that a substance is transported from the groove into the second reservoir arranged at the second section.

According to a different embodiment of the invention, at least in the area of its marginal section adjoining the piercing element the passage opening is restricted by a elastic material. For example, the elastic material is part of a elastic element arranged at or in the second section of the connection device. Said elastic element forms an opening that represents a portion of the passage opening. In the first position of the piercing element, the channel is closed by the elastic element. When the piercing element is designed at least in sections in the form of a hollow body or a tube, the exit opening of the channel is closed or covered by the elastic element.

In particular, a section of the elastic element forms the marginal section of the passage opening adjoining the piercing element, wherein in the first position of the piercing element the exit opening of the piercing element is covered by this section or the exit opening is situated on a side of the portion of the elastic element facing the first section of the connection device. In particular, the elastic element consists of a rubbery material, especially of polyisoprene, bromobutyl or chlorobutyl.

It is possible that the piercing element is arranged and constructed in such a way, that in the first position it extends into the elastic element or through the elastic element, i.e., it penetrates the elastic element not when it has reaches the second position (the opened position), but already in the first position (the closed position).

For example, in this way it is possible to achieve the smallest possible adjusting range between the closed and the opened position. Furthermore, it becomes possible to keep the force required for moving the piercing element as low as possible because when moving the piercing element into the second position the elastic element does not have to be pierced.

In particular, the elastic element is designed in the form of a membrane through which the piercing element extends, resulting in the fact that the marginal section of the passage opening adjoining the piercing element is formed by a section of the elastic element which rests like a lip against the outer surface of the piercing element. In particular, the piercing element comprises an opening in the form of a recess in the membrane material through which the piercing element extends. For example, the elastic element comprises a (for example, central) opening which, before feeding the piercing element through, has a smaller diameter when compared with the outer diameter of the piercing element, so that, after feeding the piercing element through, the edge region of this opening is folded and rests with a certain pretension against the piercing element.

However, it is also possible that initially the membrane has no opening but the piercing element is pierced through the membrane, thus producing an opening in the membrane. For example, the membrane is a self-sealing membrane which would be closed and sealed again when the piercing element is removed.

According to a further design of the invention, the first section of the connection device is designed in the form of a cup-like receptacle, i.e., the first section comprises a side wall which, for example, runs basically parallel to the possible direction of movement (or direction of longitudinal extension) of the piercing element, as well as a bottom area running oblique or vertical to the side wall. In particular, the bottom area comprises a (for example, central) opening, which forms a portion of the passage opening; i.e., the piercing element is fed in movable fashion through the bottom area of the first section.

In particular, the opening in the elastic element, which is available in the elastic element in the shape of a recess or which can be produced by feeding the piercing element through the elastic element, forms a first portion of the passage opening and die opening in the bottom of the second portion, which aligns with the first portion. In other words, the passage opening is designed in the form of a channel and penetrates the bottom area of the first section as well as the elastic element, wherein the elastic element is arranged on a side of the bottom area facing away from the side wall of the first section (i.e., the first reservoir).

It should be noted that a guide (stabilization) of the piercing element can be set up basically via the opening in the bottom of the first section, while the elastic element has mainly a sealing function. The bottom area comprises stabilizing structures, for example, in the area surrounding the opening through which the piercing element extends, the bottom is provided with an increased thickness.

According to a different embodiment of the invention, the piercing element comprises means for increasing a friction force between an outer surface of the piercing element and a section of the seal of the first reservoir. After penetrating the piercing end of the piercing element said means come in contact with the outer surface of the piercing element. For example, the means for increasing the friction force comprise friction-enhancing structures in the outer surface of piercing element, for example in the form of a plurality of recesses and/or elevations of the outer surface (in particular in the form of roughening the outer surface).

In addition it is possible, that the means for increasing the friction force has at least in sections a friction-enhancing coating arranged at the outer surface of the piercing element. For example, the means for increasing the friction force are designed in such a way that, depending on the material of the seal of the piercing element, the friction force occurring between the seal and the outer surface of the piercing element is greater than a friction force between the above-mentioned elastic element and the outer surface of the piercing element. This ensures that when the first reservoir is removed from the first section of the connection device the piercing element the piercing element is returned to its first position and the second reservoir is closed.

In a further embodiment of the invention, the piercing element comprises at least one discharge opening. In particular, the discharge opening is inserted in a casing of a piercing element formed at least in sections as a hollow body, preferably in a piercing element that is designed as a hollow cylinder. In one embodiment, the discharge opening is arranged in the piercing element in such a way that in the second position of the piercing element, in which a flow connection is possible between the first and the second section, it is located at least in sections in the interior of a reservoir arranged at the first section. For example, arranging a discharge opening or a plurality of discharge openings in the piercing element has the effect that it is possible to keep the remaining amount in a vial, which can be positioned as a reservoir at the first section, at a low level.

In particular, the piercing element can be integrally formed, for example, from a plastic material. Moreover, as described above, the piecing element can comprise at its piercing end a needle to facilitate the penetration of the seal of the first reservoir.

However, its other end is not provided with a needle, wherein this end can have a larger outer diameter than the piercing element. The larger outer diameter is located at the first position of the piercing element, for example, in an above-mentioned passage opening of the connection device and there especially in the area of an above-mentioned elastic element, wherein the best possible sealing between the piercing element and the elastic element is achieved because the marginal section of the elastic element comes in contact with the area of the larger outer diameter.

As has been explained above, the piercing element comprises in particular a longitudinal, for example, basically cylindrical form, wherein it is arranged in movable fashion along the longitudinal axis. However, the invention is certainly not restricted to a specific geometric design of the piercing element. For example, the piercing element can also have a cylindrical, triangular, cross or star-shaped cross-section.

The invention concerns also an arrangement consisting of a connection device (described above), as well as a first reservoir arranged at the first section of the connection device and/or a second reservoir arranged at the second section of the connection device.

Subsequently, the invention is explained in more detail by means of embodiments shown in the figures.

BRIEF DESCRIPTION OF THE FIGURES

FIG. 2A a sectional view of a connection device shown in FIG. 1A with a first reservoir arranged at its first section;

FIG. 2B a first perspective view of the connection device shown in FIG. 2A;

FIG. 2C a second perspective view of the connection device shown in FIG. 2A;

FIG. 2D a perspective view of the piercing element of the connection device shown in FIG. 2A;

DETAILED DESCRIPTION

Figure 1A:
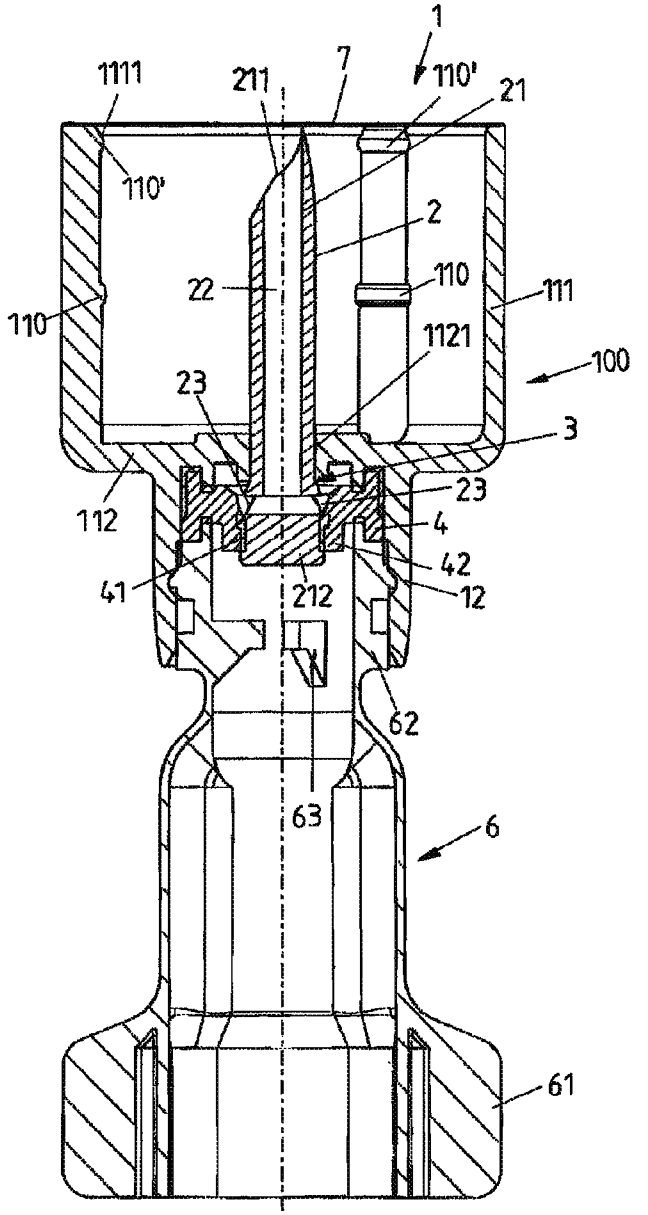
FIG. 1A a sectional view of a connection device according to a first embodiment of the invention.
Figure 1B:
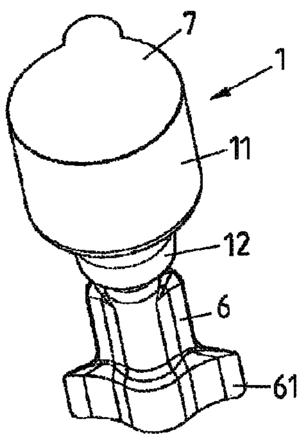
FIG. 1B a perspective representation according to a first view of the connection device shown in FIG. 1A.
Figure 1C:
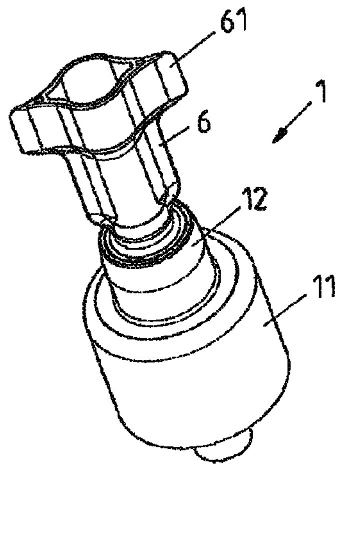
FIG. 1C a perspective representation according to a second view of the connection device shown in FIG. 1A.

The invention-based connection device 1 shown in FIG 1A comprises a first (upper) section 11 for arranging a (not shown in FIG. 1A) first reservoir in the form of an active substance container, as well as a second section 12 for arranging a second reservoir (not shown) in 5 (FIG. 2A) the form of a bag, for example, in the form of an infusion bag. The first and the second section 11, 12 are integrally connected with one another, i.e., they are designed as an integrally formed adapter part, consisting, for example, of a plastic material such as polypropylene or polycarbonate. However, it is not necessarily required to design the first and the second section as an integral part. It is also possible to form the first and the second section as separate parts which are interconnected via connection means.

In addition, the connection device 1 comprises a longitudinal piercing element in the form of a hollow needle 2. The hollow needle 2 has a piercing end in the form of a needle point 21, by means of which the hollow needle 2 penetrates the seal of a medication container, when said container is inserted into the first section 11 of the connection device (see FIG. 2A).

Furthermore, the hollow needle 2 is arranged in a passage opening 3 of the connection device in such a way that it can be moved in axial direction from a first position shown in FIG. 1A into a second position (FIG. 2A). In the first position the hollow needle 2 blocks a flow connection between the first section 11 and the second section 12, i.e., the connection device is closed. For example, this prevents that liquid (or any other substance contained in the second reservoir) escapes from the second reservoir which has been attached before the active substance container is arranged at the second section 12 of the connection device.

If the active substance container 5 is inserted in the first section 11 of the connection device 1 designed in the form of a cup-like receptacle, the needle point 21 pushes against the seal 51 of the active substance container 5 or partially penetrates the seal 51. In addition, because of the contact the seal 51 has with the outer surface of the hollow needle when the active substance container 5 is moved, the hollow needle 2 is pushed in the direction of the second section 12 (i.e., downward) into a second position, as shown in FIG. 2A.

The second position of the hollow needle 2 is defined by a limit stop 63 of the second section 12, wherein the hollow needle is pushed against the limit stop 63 by means of the movement of the active substance container 5. When the active substance container 5 is moved further after the hollow needle has come in contact with the limit stop 63, the seal 51 is completely penetrated by the hollow needle 2, thus producing a flow connection between the active substance container and the hollow needle.

It should be noted that it is also possible that the seal 51 of the active substance container is completely penetrated by the hollow needle even before the hollow needle comes in contact with the limit stop 63, wherein a movement of the hollow needle into the second position takes place especially because of the friction between the outer surface of the hollow needle and the section of the seal 51 adjoining the outer surface of the hollow needle.

In this second position there exists a flow connection between the first section 11 and the second section 12. As a result, active substance from the active substance container 5 is transported via the hollow needle 2 into a second bag arranged at the second section 12 of the connection device, or conversely that a substance contained in a bag arranged at the second section can be transported into the active substance container, in order to dissolve, dilute or mix the active substance. Consequently, in the second position of the hollow needle the connection device is opened.

As mentioned previously, the first section 11 of the connection device has a cup-like design, i.e., it comprises a side wall 111, as well as a bottom area 112, which basically runs vertically to the side wall. The first section can have a latch position and an end position (activation position) (see below). It is certainly not required that the bottom area is planar, for example, it can also be curved. The bottom area 112 involves a central opening 1121, which forms a portion of the passage opening 3 and has the purpose of guiding the hollow needle 2. To be able to achieve the most stable guidance of the hollow needle, the bottom area 112 has a thickening which surrounds the opening 1121 in ring-like fashion.

The second section 12 of the connection device 1 basically has the shape of a hollow cylinder, wherein a elastic element in the form of a membrane 4 is arranged in an intermediate area of the adapter part 100 between the first and the second section, for example, it is clamped or firmly bonded with the adapter part 100. The membrane 4 comprises a central opening 41, aligned with the opening 1121 of the first section 11, which represents a second portion of the passage opening 3. A section 42 of the membrane 4, which closely rests like a lip (bent away from the remaining membrane) against the outer surface of the hollow needle 2, forms a marginal section of the passage opening 3.

Because of the section 42 resting against the outer surface of the hollow needle, it is possible that the hollow needle 2 is clamped, which does not prevent its axial movement in the passage opening, but it can prevent an involuntary slipping of the hollow needle in the direction of the second section 12 of the connection device. In addition, the membrane seals the connection device (see description below).

It should be noted that it is possible that the opening 41 in the membrane 4 is already present in the form of a recess before the piercing element is put in place. However, it is also possible that the membrane initially had a continuous design and the membrane was penetrated by the piercing element.

The hollow needle 2 comprises a channel 22 designed as a cavity which extends from an entry opening 211 arranged in its needle point 21 to two exit openings 23 which are arranged on radially opposite sides.

The exit openings 23 shown in the embodiments presented in FIGS. 1A and 2A basically run radially or vertically to the longitudinal direction of the hollow needle 2. However, it is also possible to provide in addition or alternatively exit openings with different designs, for example, exit openings that mainly extend along the main extension direction of the hollow needle 2.

Moreover, the end 212 of the hollow needle 2 facing away from the needle point 21 has a larger outer diameter than the region of the needle point 21 or the section of the hollow needle arranged in the opening 1121 of the first section 11. In the first position of the hollow needle 2, the marginal section 42 of the membrane 4 comes in contact with the end region 212. As a result, the exit openings 23 are located above the adjoining marginal section 42, i.e., on a side facing the needle point 211 (or the first section 11), which blocks the flow connection between the first and the second section 11, 12 via the cavity 21 of the hollow needle 2 and the exit openings 22.

It should be noted that the exit openings are located below the bottom 112 of the first section and, consequently, when the hollow needle is blocked, a certain flow connection exists between the first section and the area of the adapter part 100 between the bottom 112 and the adjoining marginal section 42. This area does not belong to the "second section" 12 of the connection device, which starts below the position of the exit openings (in relation to the first position of the hollow needle), in particular below the membrane 4.

When, as is shown in FIG. 2A, during the process of inserting the active substance container 5 the hollow needle 2 is moved into the second position, the exit openings 22 enter into the second section 12, i.e., they are then situated below (on a side facing away from the needle point 21) the adjoining marginal section 42 of the membrane 4, forming via the exit openings 22 a flow connection between the first and the second section 11, 12.

As shown in FIG. 2A, after the active substance container 5 has been put in place, the needle point 21 and thus the entry opening 211 of the hollow needle 2 have penetrated the seal 51 of the active substance container 5 and is now situated in the interior of the active substance container 5. As a result, via the hollow needle 2 a flow connection is formed between the active substance container 5 and a bag arranged at the second section 12 (not shown).

According to FIG. 1A, the second reservoir, i.e., the not displayed medical bag, is arranged at the second section 12 by means of a further element in the form of an adapter 6, which is arranged at the second section 12 of the connection device 1. Said adapter 6 comprises at its end facing away from the connection device 1 wing-like arms 61 auf, which can be inserted into an opening of the bag and the bag can be connected (for example, heat-sealed or glued) with the arms 61 or with an area above the arms. At its end 62 facing away from the arms 61, the connection device 6 comprises connecting structures, for example, latching structures, by means of which it is connected with the second section 12 of the connection device 1. In addition, by locking the adapter 6 with the connection device 1, the membrane 4 is clamped in such a way that the membrane 4 achieves also a seal between the adapter 6 and the connection device.

Furthermore, even the first section 11 of the connection device comprises structures by means of which the active substance container 5 can be detachably connected with the first section, or said structures prevent at least that the active substance container slips out upward (i.e., opposite to the inserting direction). These structures comprise projections 110, which are situated at the inner surface of the side wall 111 and protrude to the inside and after inserting the active substance container they can engage an edge of its neck. The active substance container 5 is pushed into the first section in such a way that the edge of its neck is situated below the projections (end position). For example, the active substance container is pushed in to the extent that the neck (or head) attaches to the bottom 112 of the first section.

Moreover, projections 110' are also present at an edge of an opening 1111 of the first section 11, through which the active substance container 5 is inserted into the first section 11, wherein the active substance container 5 can be arranged also in a standby position at the first section 11, in which the neck of the container (especially a projection 52 of the neck) is located between these projections 110' and the projections 110 situated further down. In particular, in the standby position the hollow needle 21 is not yet pushed completely into the second position, resulting in the fact that the flow connection to the second reservoir is still blocked. Only when the medication container is pushed further down into the end position, the hollow needle is moved into the second position.

The projections 110' can also be used to bring the first reservoir after usage (i.e., from the second position) into the standby position, wherein through the movement of the first reservoir into the standby position the piercing element is taken back into the first position, thus interrupting the flow connection between the first and the second reservoir.

In addition, provision can be made to close the opening 1111 by means of a seal in the form of a membrane or a plastic film 7 in order to keep the connection device as sterile as possible. Before inserting the active substance container 5, the plastic film 7 is being removed. For example, the plastic film 7 consists of a metal or plastic film (consisting, for example, of aluminum or polypropylene).

The limit stop 63 restricting the longitudinal downward movement of the hollow needle 2 is provided by the adapter 6 which is connected with the second section 12. However, it is also possible that such a limit stop is in particular integrally formed with the second section 12 of the connection device.

When the active substance container inserted in the first section is moved upward (opposite to the direction of insertion or away from the second section 12), the hollow needle is taken upward because of the friction between the pierced seal 51 of the active substance container and the outer surface of the hollow needle 21. As a result, the hollow needle 21 returns to locking position when the active substance container is moved far enough away from the second section 12, for example, removed from the first section 11 (i.e., completely separated from the connection device), or when it is brought into the standby position.

In the area of the exit openings 23, the hollow needle 2 comprises a tapered section which expands 211 away from the needle point and which is designed in such a way that it is impossible to pull the hollow needle 2 beyond the first position out of the passage opening 3. In particular, the tapered area of the hollow needle 2 comprises a collar (see FIGS. 3A-D), which has an outer diameter that is larger than the diameter of the opening 1121 of the bottom area 112 of the first section 11. As a result, when the hollow needle is pulled out of the second position, the collar comes in contact with the edge of the opening 1121. In particular, the collar rests against the edge of the opening when the hollow needle is in its position (the locking position).

As shown in FIG. 2D, the hollow needle 2 can have structures at its outer surface which structures increase friction between a section adjoining the outer surface of the seal 51 of the active substance container 5, so that the friction toward the adjoining section of the seal within the area of the friction-enhanced area is greater that outside of the friction-enhanced area.

For example, the friction-enhanced area of the outer surface of the hollow needle 2 has a plurality of intersecting recesses 2100 or elevations. It is also possible that in addition or alternatively the outer surface is merely roughened or provided with a coating which has an increased friction coefficient to the material of the seal 51 of the container compared to the outer surface of the hollow needle. In particular, the friction-enhanced area of the outer surface of the hollow needle has a friction coefficient that is greater than the friction coefficient between the section of the outer surface of the hollow needle, on which the above-mentioned section 42 of the elastic element rests when the hollow needle is in the second position. Consequently, when the active substance container 5 is moved from the end position (FIG. 2A) upward the hollow needle 2 is also taken upward and returned into its first position.

In particular, the friction-enhancing structure or coating extends only outside of the area of the hollow needle 2, which is in its second position in contact with the marginal section 42 of the elastic element 4. Of course, the friction-enhancing structure or coating is optional. By moving the active substance container from the first section into the first position the hollow needle can be taken along without using friction-enhancing means.

FIGS. 3A to 3D provide a detailed view of the hollow needle 21 shown in FIGS. 1A *and* 2A. In particular, it is shown that the exit openings 23 are arranged in a tapered section 210, which tapers in the direction of the needle point 21. The tapered section 210 extends between a first hollow cylindrical area 240 and a second hollow cylindrical area 250, which forms the second end 212 of the hollow needle 21 and which has a greater outer diameter than the first hollow cylindrical area 240.

Between the tapered area 210 and the second section 250 there is a collar 255, which has an even greater outer diameter than the second section 250 and which pushes in the first position of the hollow needle 2 (see FIG. 1A) into the marginal section 42 of the elastic element 4.

Figure 3A:
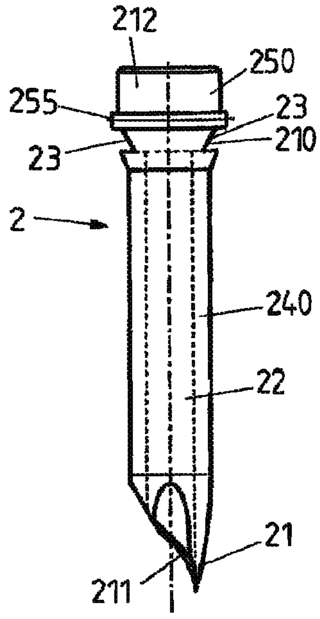
FIG. 3A a lateral view of the piercing element of the connection device shown in FIG. 1A.
Figure 3B:
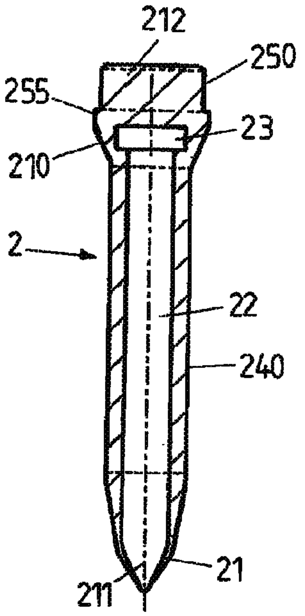
FIG. 3B a lateral view of the piercing element shown in FIG. 3A.
Figure 3C:
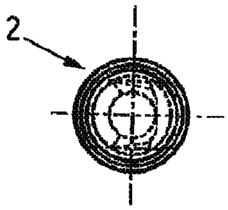
FIG. 3C a lateral view of the piercing element shown in FIG. 3A vertically to its longitudinal direction.
Figure 3D:
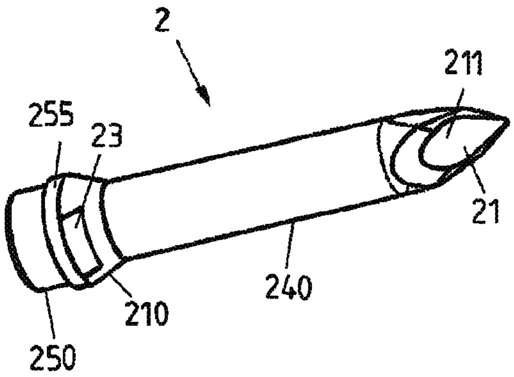
FIG. 3D a perspective view of the piercing element shown in FIG. 3A.

According to FIG. 3B, in a cut along a plane running parallel to the longitudinal axis of the hollow needle, the exit openings 23 have an at least almost rectangular cross section. However, as mentioned above, it is also possible to use different embodiments of the exit openings. The end 212 of the hollow needle 2 opposite to the needle point 21 forms a closed end, so that in the second position of the hollow needle (FIG. 2A) the flow connection between the active substance container and the second reservoir is formed only via the entry opening 211, the cavity 22, as well as the exit openings 23.

Figure 4A:
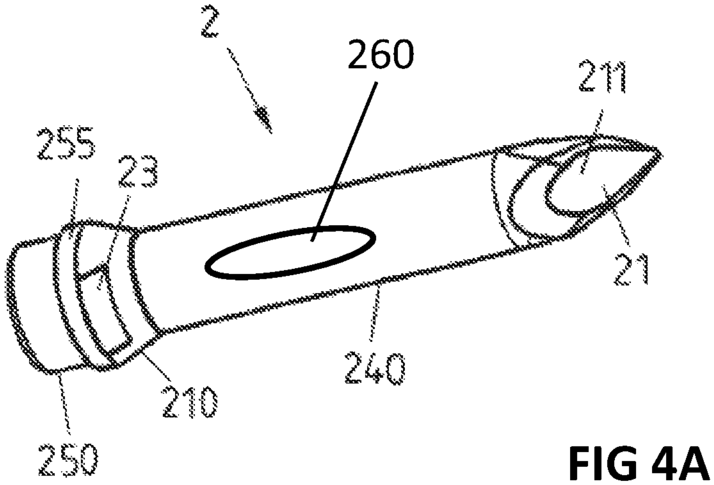
FIG. 4A the perspective view of the piercing element shown in FIG. 3D with a discharge opening.
Figure 4B:
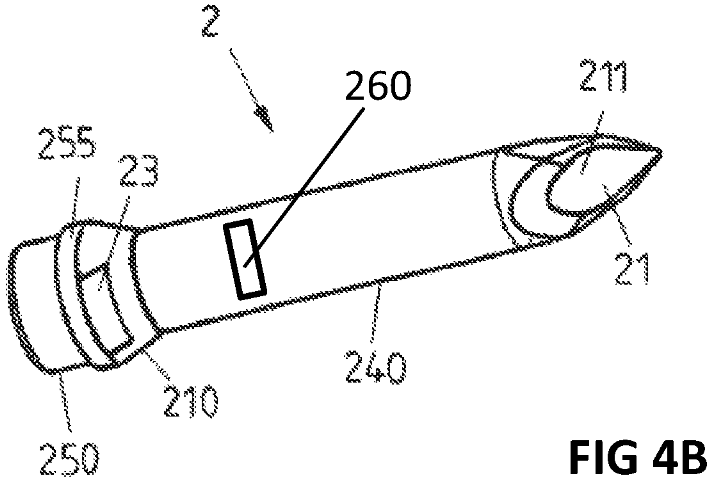
FIG. 4B the perspective view of the piercing element shown in 4A with a further embodiment of a discharge opening.
Figure 4C:
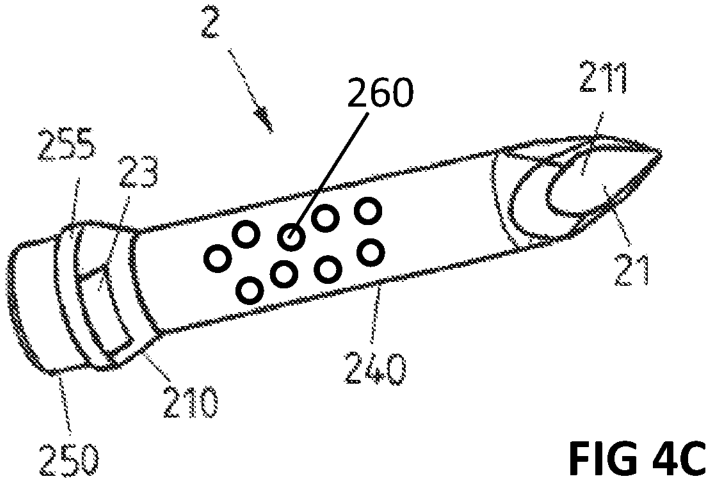
FIG. 4C the perspective view of the piercing element shown in 4A with a plurality of discharge openings.

Each of piercing elements 2 shown in FIGS. 4A to 4C has a different embodiment of a discharge opening 260. A discharge opening 260 represents a passage through which the content, for example, a liquid, of the first reservoir is transported in the direction of the second reservoir or vice versa. The discharge openings 260 are inserted in the casing of the piercing element 2. They are positioned between the entry opening 211 and the exit opening 23. They can have different shapes and/or sizes.

For example, FIG. 4A shows a discharge opening 260 having a longitudinal shape, which extends along the longitudinal axis of the piercing elements 2. FIG. 4B also shows a discharge opening 260 with longitudinal shape, but it extends transversely to the longitudinal axis of the piercing element 2. The length of a discharge opening 260 can comprise a magnitude of between 5 mm and 15 mm. FIG. 4C shows a plurality of small, for example, round discharge openings 260.

Figure 5A:
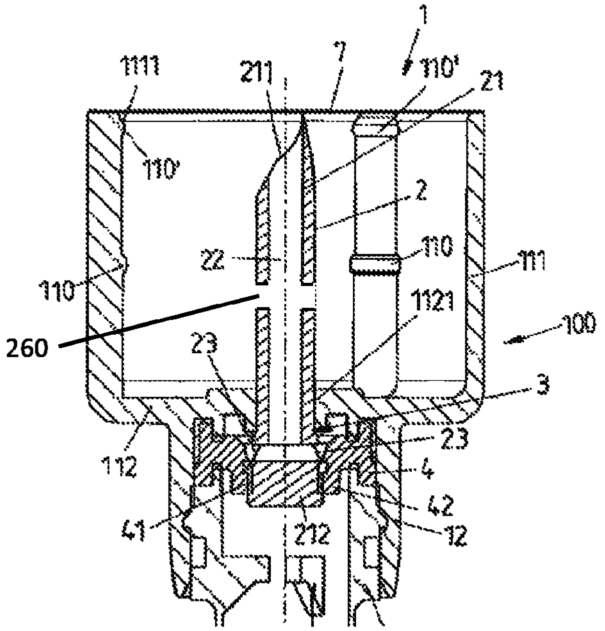
FIG. 5A a sectional view of the connection device shown in FIG. 1A with a piercing element and inserted discharge openings in locking position.
Figure 5B:
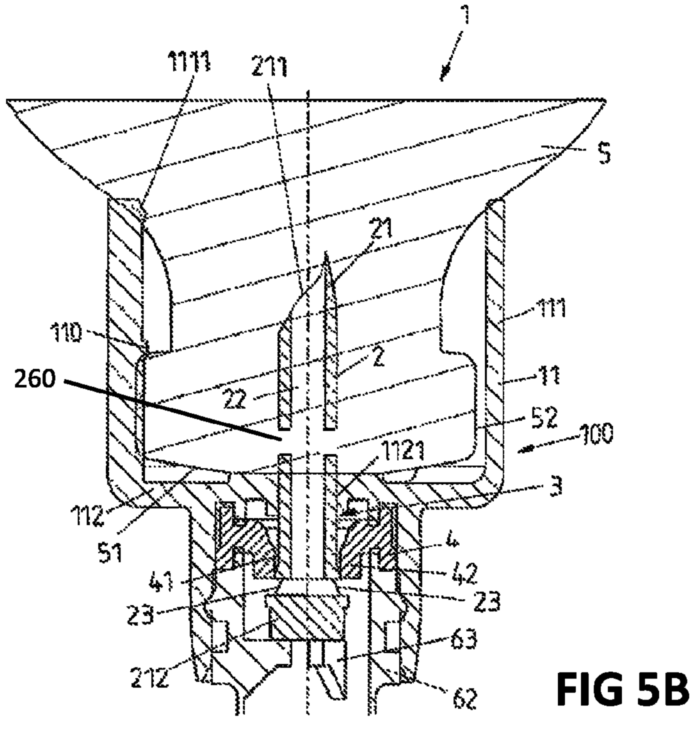
FIG. 5B a sectional view of the connection device shown in FIG. 5A with a reservoir and the piercing element and the inserted discharge openings in closed position.

In conclusion, in order to demonstrate the performance of the discharge openings 260, FIGS. 5A and 5B show the connection device 1 without a connected reservoir 5 and the piercing element 2 in its first position, in which the channel, here the exit opening 23 of the channel, is closed (FIG. 5A) and with a connected reservoir 5 and the piercing element 2 in its second position, in which the channel, here the exit opening 23 of the channel, is open or released (FIG. 5B). The discharge openings 260 are inserted above the exit opening 23 in the casing of the piercing element 2. The discharge openings 260 are displaced or arranged upward along the longitudinal axis of the piercing element 2, in the direction of the entry opening 211, to the extent that they are allocated to the interior of the vial 5 when the vial (as an example for a reservoir 5) is inserted and the piercing element is pushed down 2. The discharge openings extend at least in sections, preferably completely, into the interior of the vial 5. The amount in the vial 5 remaining below the entry opening 211 of the piercing element 2 could not be discharged from the vial 5 without the discharge openings 260 and could therefore not be used. By means of the discharge openings 26, it is possible to keep the amount remaining in the connected vial 5 as low as possible. The position of the discharge openings 260 in the piercing element 2 is selected in such a way that the discharge openings 260 are located at least in sections, preferably completely, above the seal 51, in particular above the washer of the seal 51. Preferably, the discharge openings 260 adjoin the washer of the seal 51.

REFERENCE LIST

1 Connection device
2 Hollow needle
3 Passage opening
4 Membrane
5 Active substance container
6 Adapter
7 Plastic film
11 First section
12 Second section
21 Needle point
22 Cavity
23 Exit opening
41 Opening
42 Marginal section
51 Seal
52 Projection
61 Arm
62 End
63 Limit stop
100 Adapter part
110, 110' Projection
111 Side wall
112 Bottom area
210 Tapered area
211 Entry opening
212 End
240 First section
250 Second section
255 Collar
260 Discharge opening
1111 Opening
1121 Opening bottom area
2100 Recess

The invention claimed is:

1. Connection device for connecting a first reservoir with a second reservoir, the connection device comprising a first section configured to receive a first reservoir closed with a seal;

a second section connected to the first section; and a piercing element, which penetrates with a piercing end the seal of the first reservoir when the first reservoir is arranged at the first section, wherein the piercing element including a piercing end, a proximal end and a channel and can be moved from a first position into a second position, wherein in the first position the channel of the piercing element is closed and a flow connection between the first and the second section is blocked, while in the second position the channel of the piercing element is released and a flow connection between the first and the second section is made possible; and an adapter disposed within the second section and having a first end configured to contact the proximal end of the piercing element and a second end for receiving the second reservoir.

2. Connection device according to claim 1, wherein the piercing element is moved into the second position when as a result the first reservoir is arranged at the first section, that the piercing element is brought into an end position relative to the first section, wherein the piercing element is designed and arranged in such a way that the piercing element can be returned into the first position when the first reservoir is moved from the end position and away from the second section of the connection device.

3. Connection device according to claim 1, wherein the piercing element is arranged in movable fashion in a passage opening relative to the first and the second section.

4. Connection device according to claim 3, wherein via the channel in the second position of the piercing element a flow connection is formed between the first and the second section of the connection device, wherein in the first position of the piercing element a marginal section of the passage opening adjoins the piercing element and blocks a flow connection via the channel between the first and the second section.

5. Connection device according to claim 4, wherein the channel is designed in the form of a cavity extending in the interior of the piercing element, which channel runs from an entry opening located in the area of the piercing end to at least one exit opening.

6. Connection device according to claim 5, wherein the exit opening is arranged in such a way that in the first position of the piercing element is the piercing element located on a surface of the marginal section of the passage opening facing the piercing end and in the second position of the piercing element is the piercing element located on a surface of the marginal section of the passage opening facing away from the piercing end.

7. Connection device according to claim 6, the piercing element is designed in the form of a hollow body, and the exit opening runs basically in radial direction, wherein the end of the piercing element spaced from the piercing end is closed.

8. Connection device according to claim 1, wherein the channel is formed as a recess in an outer surface of the piercing element.

9. Connection device according to claim 3 at least in the area of its marginal section the passage opening, which closes the channel of the piercing element when the piercing element is in the first position, is restricted by an elastic element.

10. Connection device according to claim 9, in the first position the channel of the piercing element is closed through the elastic element.

11. Connection device according to claim 9, wherein in the first position the piercing element extends into the elastic element or through the elastic element.

12. Connection device according to claim 9, wherein the channel is designed in the form of a cavity extending in the interior of the piercing element, which channel runs from an entry opening located in the area of the piercing end to at least one exit opening, the marginal section of the passage opening adjoining the piercing element is formed by a section of the elastic element, wherein in the first position of the piercing element the exit opening is closed by said section or the exit opening is situated on a side of said section of the elastic element facing the first section of the connection device.

13. Connection device according to claim 11, wherein the piercing element runs through the elastic member and the section adjoining the piercing element is formed by a section of the elastic member, which rests like a lip against the outer surface of the piercing element.

14. Connection device according to claim 13, the piercing element runs through an opening formed in the elastic member in the form of a recess or is pierced through an originally continuous section of the elastic member.

15. Connection device according to claim 3, wherein the first section is formed in the form of a cup-like receptacle and a bottom of the first section has an opening, which forms a section of the passage opening.

16. Connection device according to claim 1, wherein the piercing element comprises means for enhancing a friction force between an outer surface of the piercing element and a section of the seal of the first reservoir, which after penetrating the piercing end of the piercing element adjoins the outer surface of the piercing element, the means for enhancing the friction force including a friction-enhancing coating arranged at the outer surface of the piercing element.

17. Connection device according to claim 1, wherein the adapter comprises a limit stop, which defines the second position of the piercing element.

18. Connection device according to claim 1, wherein the piercing element comprises at least one discharge opening.

19. Connection device according to claim 18, wherein the discharge opening is inserted in a casing of a piercing element which is designed at least in sections as a hollow body.

20. Connection device according to claim 18, wherein the discharge opening is arranged in the piercing element in such a way, that when the piercing element is in the second position, in which a flow connection is made possible between the first and the second section, the discharge opening located at least in sections in an interior of a reservoir arranged at the first section.

21. Connection device according to claim 1, wherein the adapter includes arms configured to connect to an opening of the second reservoir.

22. Connection device of claim 21, wherein the arms are configured to be glued or heat-sealed to the opening of the second reservoir.

23. Connection device of claim 16, wherein the means for enhancing the friction force includes a roughing of the outer surface of the piercing element.

* * * * *